United States Patent [19]

Petersen

[11] Patent Number: 4,706,660

[45] Date of Patent: Nov. 17, 1987

[54] PATELLAR CLAMP

[76] Inventor: Thomas D. Petersen, 5555 Reservoir Dr., San Diego, Calif. 92120

[21] Appl. No.: 857,194

[22] Filed: Apr. 29, 1986

Related U.S. Application Data

[62] Division of Ser. No. 739,153, May 30, 1985, Pat. No. 4,633,862.

[51] Int. Cl.$^4$ .................................. A61F 5/04
[52] U.S. Cl. ........................ 128/92 VW; 128/92 VZ; 81/361
[58] Field of Search ............ 128/316, 330, 329, 92 R, 128/92 V, 92 VY, 92 VW, 92 VZ; 623/20; 40/300, 301; 81/355, 356, 361

[56] References Cited

U.S. PATENT DOCUMENTS

| | | | |
|---|---|---|---|
| 242,860 | 6/1881 | Barnes | 128/316 |
| 339,526 | 4/1886 | Butterworth | 128/316 |
| 1,667,563 | 4/1928 | Perrin | 81/361 |
| 2,082,669 | 6/1937 | Voigt | 81/361 |
| 3,605,310 | 9/1971 | Brown | 40/301 |
| 4,147,168 | 4/1979 | Hayes et al. | 128/316 |
| 4,285,070 | 8/1981 | Averill | 623/20 |

FOREIGN PATENT DOCUMENTS

| | | | |
|---|---|---|---|
| 90048 | 8/1921 | Switzerland | 128/330 |
| 195287 | 3/1923 | United Kingdom | 128/330 |

OTHER PUBLICATIONS

Sales Catalog 17, "Microloc" Porous Coated Knee System and Surgical Technique Johnson & Johnson Inc. Ortho Div.

"Zimmer" Intramedulary Knee Instrumentation for the Miller/Galante Total Knee System, Sales Catalog, Zimmer, Inc. copyright 1986.

Primary Examiner—C. Fred Rosebaum
Assistant Examiner—Ralph Lewis
Attorney, Agent, or Firm—Sherman and Shalloway

[57] ABSTRACT

Disclosed herein is a patellar clamp which includes a fixed jaw having a spike centrally disposed on a part spherical surface with this spike being axially aligned with a reciprocating plunger. The plunger is operated by a second handle pivotably disposed with respect to the first handle and spring biasing means between the handles biases them in a direction of separation of the plunger and spike. The inventive patellar clamp is utilized to install a patellar button onto a resected patella.

6 Claims, 9 Drawing Figures

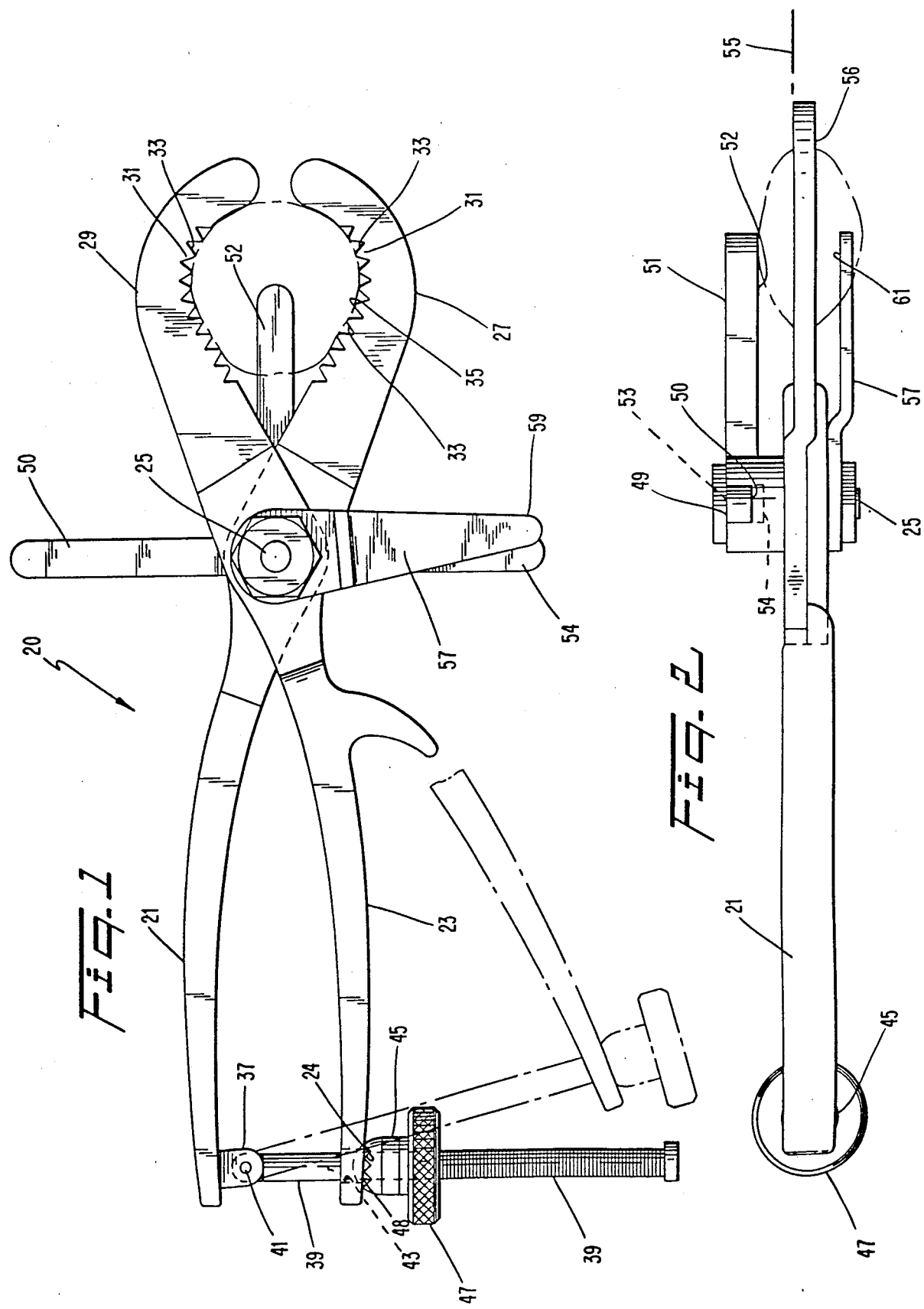

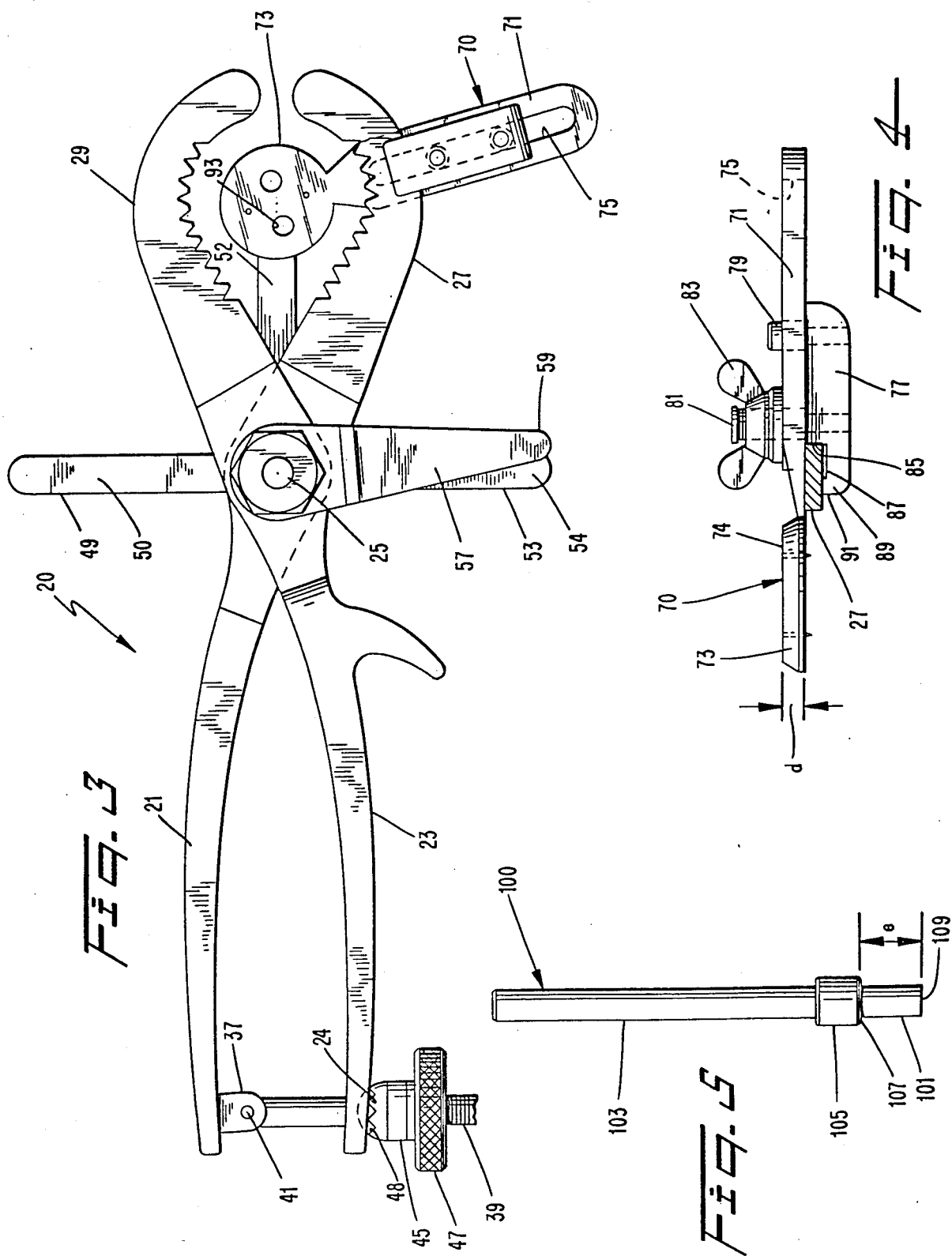

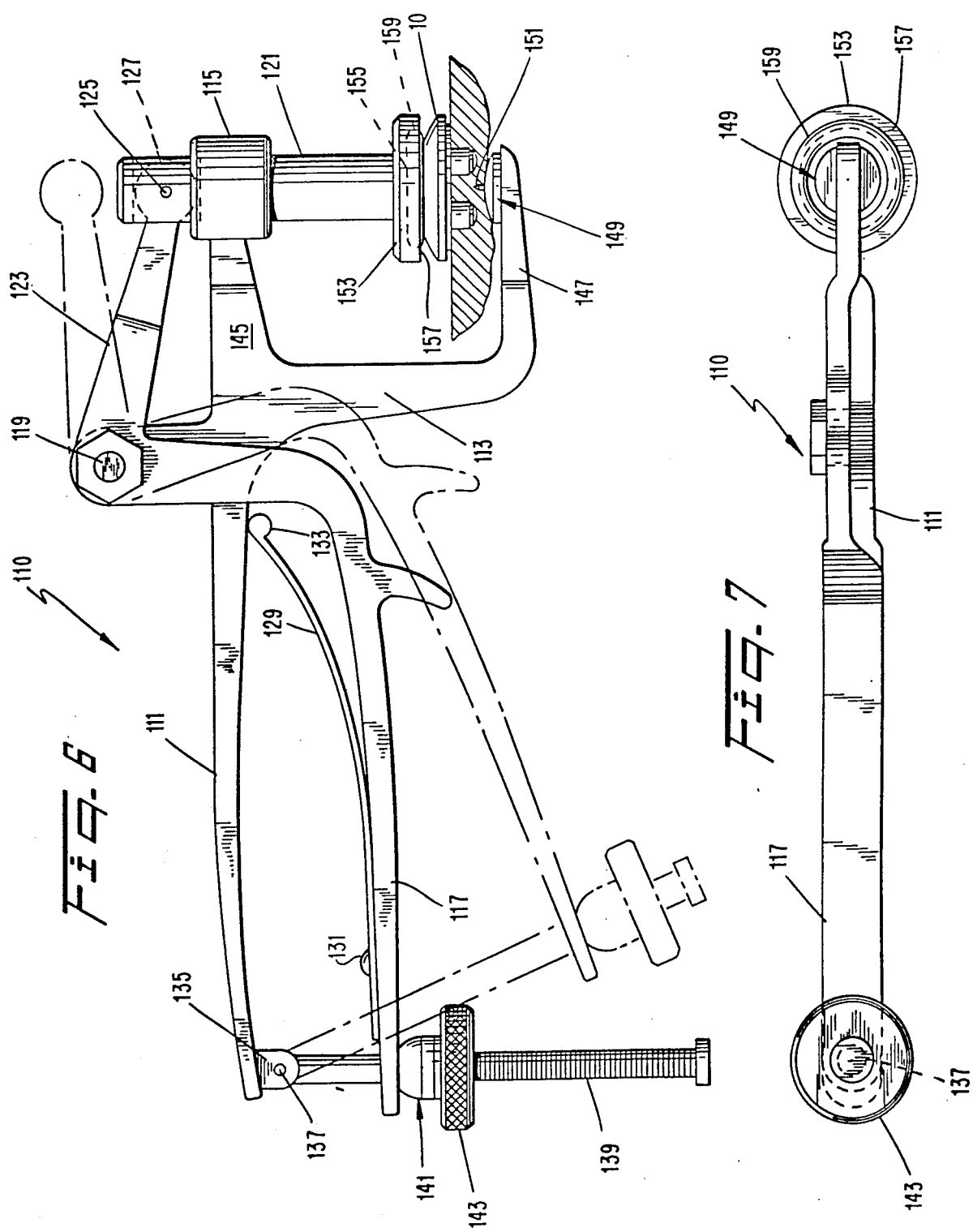

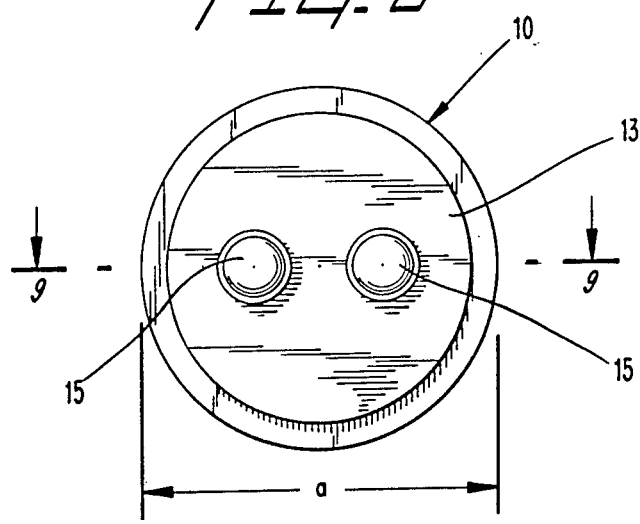
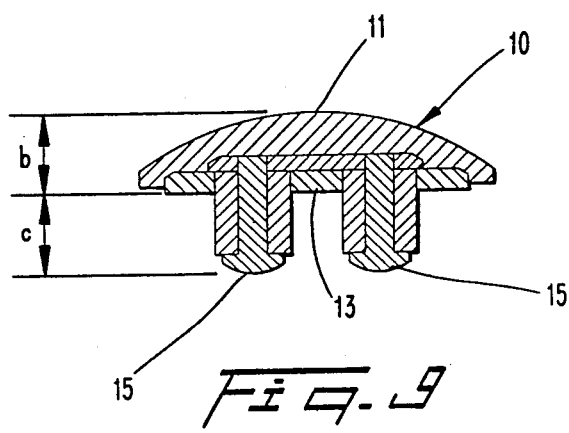

PATELLAR CLAMP

This is a division of application Ser. No. 739,153, filed May 30, 1985 now U.S. Pat. No. 4,633,862.

BACKGROUND OF THE INVENTION

The present invention relates to a method and instruments for installation of a patellar button prosthesis. In the prior art, it is known to resect the patella for the purpose of installation of a patellar button prosthesis. Heretofore, no system of instruments has been developed which enables the surgeon to accurately take into account all parameters of surgery which must be taken into account in order to perform the surgery in a satisfactory matter. Such aspects of surgery as ensuring that adequate bone stock will remain after resection and that holes drilled in the patella will not be unduly deep in light of the amount of remaining bone stock have not to this time been taken into account in the design of instruments for performing such surgery. Further, to this time, instruments have not been provided for this type of surgery which are flexible enough to be utilized in a satisfactory manner for patellar buttons of different sizes and configurations.

The following prior art is known to Applicant:

The following prior art references are believed to be of general interest concerning the inventive saw guide:

U.S. Pat. No. 966,500 to Wegner discloses a combined holder and centering tool which is best seen in FIG. 1 to include a pliers-like device including jaws 5 and 6 and further including a centering tool 8 pivotally mounted on a common axis with the axis of rotation of the jaws 5 and 6 and having an end 9 with a centering hole 10 therein which is provided to center a boring tool. While some general analogy may be drawn between the centering tool 8, 9, 10 of Wegner and the drill guide of the present invention, it must be noted that the centering tool of Wegner is extremely limited in that it may only center the boring tool along an arc defined by the length of the portion 8 and the axis of rotation thereof. In contradistinction to this, the drill guide of the present invention may be located anywhere along the saw guide jaws where desired and thus provides infinite adjustability of the location of the centering holes thereof. This patent is believed to be only generally relevant as showing the combination of a pliers-like instrument and a drill guide.

U.S. Pat. No. 3,035,581 to Bonta discloses a power driven surgical knife having a guide bar laterally spaced from the blade for aiding in determining the thickness of the cut. This is believed to differ from the inventive saw guide in that as explained hereinafter, the surgeon cuts the patella along a plane defined by one side of the jaws of the saw guide which jaws remain stationary during the cut. In Bonta, the guide thereof moves with the blade thereby causing instability during the resection process.

U.S. Pat. No. 4,457,307 to Stillwell discloses a bone cutting device for total knee replacement which includes an assembly for mounting to the femur which has pivotally and longitudinally attached thereto a carriage carrying a power saw. The power saw disclosed in Stillwell may if desired, be usable with the present invention and if so used, the power saw blade would be aligned with the posterior edge of the jaws of the saw guide of the present invention. The details of the device disclosed by Stillwell are accordingly only believed to be of general interest concerning the teachings of the present invention.

Regarding the inventive drill guide, the following references are believed to be generally related thereto:

U.S. Pat. Nos. 2,181,746 and 2,291,413, both to Siebrandt disclose combination bone clamps and adjustable drill guides. These devices are believed to be of only general interest concerning the present invention in that the drill guides of the Siebrandt patents are oriented substantially perpendicular to the orientation of the drill guides of the present invention. The Siebrandt drill guides rely upon holes formed in one of the jaw members of the related bone clamp for their operation whereas in the present invention, the only holes are formed in the drill guide itself which is slidably mountable on one of the jaws and includes a drill guide portion which protrudes over the opening formed by the inner surfaces of the jaws when closed about the patella.

U.S. Pat. No. 3,804,546 to Boyajian discloses a drill guide including adjustability thereof enabling pivoting and rotation thereof with respect to its handle. There is no means disclosed in Boyajian to attach the drill guide to a jaw of an associated saw guide, and as such, this patent is believed to be of only general interest.

U.S. Pat. No. 3,835,849 to McGuire discloses a bone clamp and adjustable drill guide wherein a bone may be clamped between on the one hand a member 1,5,6,7 and another member designated by reference numeral 13. The member 13 also includes holes therein designated by reference numerals 24A and 30A which comprise the drill guides. This reference is believed to be of only general interest concerning the present invention in that the drill guide is integrally formed with the clamp and is thus not moveable with respect thereto.

U.S. Pat. No. 4,256,420 to Day discloses a nail head drilling guide including a handle attached to a plate through a body portion having holes 30 therein for guiding the nails. There is not believed to be any disclosure or suggestion in this patent of the attachment of the inventive guide to a jaw of a saw guide.

U.S. Pat. No. 4,421,112 to Mains, et al. discloses a tibial osteotomy guide assembly and method including a device attachable to the tibia through elongated pins and having a device 20 with bores therein which are provided so as to guide the insertion of pins into the tibia which are utilized to guide the movements of a saw. This device is believed to be of only general interest concerning the present invention in that there is no ability of the guide to be adjustable with respect to a clamping device.

U.S. Pat. No. 4,444,180 to Schneider, et al. discloses a clamp-like device wherein one of the jaws thereof comprises a drill guide. This device is believed to be of only general interest concerning the present invention since the drill guide thereof is not adjustable with respect to the jaw on which is it integrally formed.

The following prior art is believed to be generally related to the inventive patella clamp:

U.S. Pat. Nos. 339,526 to Butterworth, 2,570,048 to Cooke, et al. and 4,147,168 to Hayes, et al. all relate to tools for placing some sort of identifying mark on an animal such as a ring through the nose or an identification tag. Hayes, et al. is believed to be slightly more relevant that Butterworth or Cooke, et al. in that Hayes, et al. discloses a plunger 54 constrained to move linerally by the opening 58 formed in an elongated housing portion 60 thereof.

SUMMARY OF THE INVENTION

The present invention overcomes the deficiencies in the prior art as exemplified by the patents discussed hereinabove by providing a method and instruments for installation of a patellar button prosthesis, including the following inventive features:

(a) The present invention includes an improved patellar clamp which is utilized to enable installation of the patellar button prosthesis in its appropriate location on the resected patella. The improved patella clamp includes a pair of opposed jaws, one of which is reciprocable with respect to the other.

(b) The fixed jaw of the patellar clamp includes a fixation spike and a spherical surface surrounding the fixation spike which enables the patella to be fixed thereon in a stable position. The reciprocable jaw is constrained to linear motion by the structure of the patella clamp and includes a bottom surface engaging the patellar button prosthesis in a manner so as to ensure accuracy in installation of the patellar button prosthesis.

(c) The present invention also includes the method for installing the patellar button prosthesis onto the patella utilizing the instruments described hereinabove. Many of the details of the method should be self evident from the above description and the method will be described in greater detail hereinafter.

Accordingly, it is a first object of the present invention to provide a set of instruments which may be used in resecting a patella and installing a patella button prosthesis.

It is a further object of the present invention to provide a set of instruments which may be utilized to grasp the patella in the correct anterior to posterior position while simultaneously indicating a guide plane for the resection operation.

It is a yet further object of the present invention to provide a set of instruments which allows holes to be drilled in the resected patella while controlling both the location of the holes and the depth thereof. It is a still further object of the present invention to provide a set of instruments which allows the accurate installation of the patella button prosthesis after the resection and drilling are completed.

It is a still further object of the present invention to utilize the set of instruments in practicing the method of installing a patella button prosthesis as set forth herein.

These and other objects, aspects and features of the present invention will be better understood from reading the specific description of the preferred embodiments set forth hereinafter while referring to the appended drawing figures.

BRIEF DESCRIPTION OF THE DRAWINGS

FIG. 1 shows a top view of the saw guide of the present invention in a position grasping a patella;

FIG. 2 shows a side view of the saw guide shown in FIG. 1 and grasping the patella;

FIG. 3 shows a view similar to FIG. 1 but showing the inventive drill guide attached to one of the jaw members of the saw guide;

FIG. 4 shows a side view of the drill guide shown in FIG. 3 including details of the means attaching the drill guide to the saw guide jaw member;

FIG. 5 shows a side view of a drill bit utilized in conjunction with the drill guide to limit the depth of penetration of the drill bit into the patella;

FIG. 6 shows a side view of the patellar clamp in accordance with the present invention;

FIG. 7 shows a top view of the patellar clamp shown in FIG. 6;

FIG. 8 shows a top view of a patellar button prosthesis;

FIG. 9 shows a cross-sectional view along the line 9—9 of FIG. 8.

SPECIFIC DESCRIPTION OF THE PREFERRED EMBODIMENTS

Reference is first made to FIGS. 8 and 9 wherein is shown a patellar button prosthesis 10 which includes a top surface 11 which comprises a portion of a sphere, a substantially back surface 13, and a pair of outwardly extending posts 15. The patellar button prosthesis has a diameter designated by the letter a, a thickness designated by the letter b and the posts 15 extend outwardly from the surface 13 by distance designated by the letter c. As is known to those skilled in the art, the patellar button prosthesis 10 is available in several different sizes so as to give a surgeon flexibility in operating on patellas of different sizes. Thus, as the diameter a of the patellar button prosthesis 10 increases, a corresponding increase in the thickness b necessarily follows. These features of the patellar button prosthesis 10 will take on added significance when considered in conjunction with the specific description of the patellar instruments as set forth hereinbelow.

Referring now to FIGS. 1, 2 and 3, the inventive saw guide 20 is seen to include a first handle 21 and a second handle 23. The handles 21 and 23 are mounted in pivoting relation with respect to one another by the bolt 25 which extends through holes in the handle members 21 and 23 which are aligned for this purpose. The handle 21 has integrally formed therewith a jaw member 27 which in assembly faces a further jaw member 29 which is integrally attached to the handle member 23. As best seen in FIGS. 1 and 3, each of the jaw members 27 and 29 includes a plurality of teeth 31 formed by angled surfaces 33 and flat ends 35. If desired, the jaw members 27 and 29 may have respective grooves centrally located with respect to the anterior and posterior faces thereof so that each tooth 31 is comprised of two teeth, a first tooth adjacent the jaw member anterior faces and a second tooth adjacent the jaw member posterior faces.

With further reference to FIGS. 1 and 3, it is seen that the handle member 21 has an eyelet 37 integrally attached thereto which eyelet pivotally mounts a threaded member 39 at the pivot 41. The threaded member 39 extends through an opening 43 formed at the end of the handle member 23 and has threaded thereon a nut 45 which preferably has a knurled surface 47 so as to facilitate gripping and rotating the nut 45. The purpose for the threaded member 39 and nut 45 is to enable the locking of the position of the jaw members 27 and 29 in a pre-determined grasping relation about the periphery of a patella. Further, the nut 45 and handle member 23 have respective facing serrated surfaces 48 and 24 which enhance the retention of the nut in a particular rotative and longitudinal position with respect to the threaded member 39.

With particular reference to FIGS. 1 and 2, it is seen that the bolt 25 which carries the handle members 21 and 23 and jaw members 27 and 29 in pivoting relationship with respect to one another, also defines the pivot for a plurality of gauges provided for a purpose to be described hereinafter. On the posterior side of the saw guide 20, with the posterior side being defined as that side of the saw guide which is intended to be on the posterior side of the patella in use, three wing gauges 49, 51 and 53 are provided which as shown are fixedly spaced from one another on a single rotatable assembly. As explained hereinabove, with reference to FIGS. 8 and 9, patellar button prostheses are made in several different sizes and as the diameter a thereof increases, so does the thickness b increase correspondingly. The wing gauges 49, 51 and 53 have respective surfaces 50, 52 and 54 which face the posterior faces of the jaw members 27 and 29. As may be seen with reference to FIG. 2, the posterior faces of the jaw members 27 and 29 are in a common plane designated in FIG. 2 by the reference numeral 55. The plane 55 defines the plane of resection of the patella and FIG. 2 shows a patella as inserted and secured within the saw guide 20 and with the wing gauge 49 pivoted into a position where the surface 50 thereof is a pre-determined distance from the pane of resection 55. The wing gauge 50 has been pivoted to the position shown in FIG. 2 because the surgeon, in this example, has decided to install in the patella a patellar button prosthesis having a thickness dimension b corresponding to the distance between the surface 50 and the plane of resection 55 and having a diameter a. This will be explained in greater detail hereinafter. Thus, in the saw guide 20 as shown in FIGS. 1-3, provision is made through the inclusion therein of three wing gauges 49, 51 and 53 for the use of patellar button prostheses of three different thicknesses b respectively corresponding to (1) the distance between the surface 50 and the plane of recession 55, (2) the distance between the surface 52 and the plane of resection 55 and (3) the distance between the surface 54 and the plane of resection 55.

As further seen with reference to FIGS. 1-3, a further lower gauge 57 is provided on the anterior side of the saw guide 20. The lower gauge 57 includes an end 59 which when pivoted toward the jaw members 27 and 29 is suspended over an opening defined between the jaw members. The portion 59 includes a surface 61 which is a pre-determined distance from the posterior surfaces 55 of the jaw members 27 and 29. After the surgeon has chosen the appropriate patellar button prosthesis 10 having a thickness dimension b and has pivoted the appropriate posterior wing gauge 49, 51 and 53 into the position shown in FIG. 2 and properly grasped the patella, the lower gauge 57 is then pivoted to the position shown in FIG. 2. The distance between the surfaces 55 and 61 as seen in FIG. 2 is specifically designed so that if the lower gauge 57 is able to rotate in a complete circle without engaging the anterior surfaces of the patella, then the surgeon will know that insufficient bone stock will remain after resection. In the example shown in FIG. 2, the end 59 of the lower gauge 57 engages the anterior surfaces of the patella which indicates that sufficient bone stock will remain after resection. If the lower guide 57 is able to rotate freely, then the saw guide 20 must be repositioned posteriorly until rotation of the lower guide 57 results in engage of the end 59 thereof with the anterior surfaces of the patella. When such repositioning of the saw guide 20 is required, the surgeon must choose a different patellar button prosthesis having a thickness b which is less than the thickness b of the previously chosen patellar button 10.

After the patella has been properly positioned within the saw guide as shown in FIG. 2, with the wing gauge, in this example 49, engaging the posterior surface of the patella and the lower gauge 57 portion 59 pivoting in a manner so as to engage the anterior surfaces of the patella, the patella may then be resected along the plane 55. The handle members 21 and 23 are fixed by tightening the nut 45 in a position wherein the jaw members 27 and 29 tightly engage the periphery of the patella. Then, the saw is utilized to slice off those portions of the patella posterior of the plane 55. This is accomplished by having the saw blade engage the top surfaces of the jaw members 27 and 29 throughout the cutting motion. In this way, an accurate flat cut along the plane 55 may be accomplished.

With reference now to FIGS. 3, 4 and 5, after the patella has been resected along the plane 55, a drill guide 70 is affixed to one of the jaw members 27 and 29 so that the appropriate holes may be drilled in the patella for receipt of the posts 15 of the patellar button prosthesis 10. With reference to FIG. 3, the drill guide 70 is seen to include a handle portion 71 and a template portion 73. As shown in FIG. 3, the handle portion 71 includes an elongated groove 75 for a purpose to be described hereinafter.

With reference now to FIG. 4, it is seen that a locking member 77 is slidably mounted within the groove 75 by virtue of an upstanding post 79 and an upstanding threaded member 81, which has threadably mounted thereon a nut 83. The upstanding post 79 serves as a guide means to guide the locking member 77 in its linear motion along the groove 75 and the threaded member 81 and wing nut 83 serve to lock the locking member 77 in a pre-determined position along the path of movement along the slot 75.

As may be seen with reference to FIG. 4, the locking member 77 includes a shoulder formed by the surfaces 85 and 87 with the surface 87 being located on an elongated lip 89 extending away from the major portion of the locking member 77. At the end of the lip 89, a flat surface 91 is formed which extends upwardly toward the handle portion 71 beyond the extent of the surface 87.

With reference to FIGS. 3 and 4, the mounting of the drill guide 70 onto a jaw of the saw guide 20 should be easily understood. FIG. 4 shows a cross-section of the jaw member 27 of the saw guide 20. The drill guide 70 may be easily mounted on the jaw member 27 or the jaw member 29 by loosening the wing nut 83 thereby allowing the locking member 27 to move downwardly with respect to the handle portion 71, the locking portion 77 is slid over the jaw member, in this case 27, until the shoulder 85 thereof abuts a side of the jaw member with the surface 91 lightly engaging the underside of the jaw member. Thereafter, the wing nut 83 may be tightened so as to cause frictional engagement between the surface 91 of the locking member 77 and the surface of the jaw member with the surface 85 of the locking member 77 engaging the jaw member for added stability. From this explanation, it should be clear that the drill guide may be repositioned with respect to the jaw member to which it is releasably attached through loosening of the wing nut 83 and either sliding motion of the locking member with respect to the jaw member along its longitudinal extent, or reciprocation of the handle portion 71 with respect to the locking member 77 with no longitudinal movement of the locking member 77 with respect to the jaw member, or both motions either simultaneously or concurrently so that it should be clear that the position of the drill guide 70 is infinitely adjustable with respect to the jaw member to which it is attached.

With further reference to FIG. 3, it is seen that the template 73 includes therethrough a pair of holes 93 which serve as guides for a drill bit which may be extended therethrough so as to enable the drilling of holes in the posterior surface of the resected patella.

As shown in FIG. 4, the template 73 has a thickness designated by the letter d. With reference to FIG. 5, it is seen that the drill bit 100 which is intended to be used in conjunction with the drill guide 70 includes a drilling end portion 101 designed so as to be able to drill a hole in the patella, a stem portion 103 which is provided so as to enable attachment of the drill bit 100 to the appropriate drill and a collar portion 105 interposed between the drilling portion 101 and the stem portion 103 and having a bottom shoulder 107. The distance between the shoulder 107 and the end 109 of the drill bit is designated in FIG. 5 with the letter e and this distance is so related to the thickness d of the template 73 so as to limit in a pre-determined manner the distance to which the drilling portion 101 may penetrate the posterior surface of the resected patella. Thus, the collar 105 acts as a limit stop through the interaction of the shoulder 107 and the surface 74 of the template 73 so as to pre-determine the depth of the holes which are to be drilled in the posterior surface of the resected patella. The distance defined by subtracting the distance d from the distance e is specifically pre-determined so as to be slightly longer than the dimension c of the posts 15 as shown in FIG. 9. In this way, holes are drilled in the posterior surface of the resected patella which are sufficiently long so as to accomodate the patellar button prosthesis 10 with the surface 13 thereof bearingly engaging the flat posterior surface of the resected patella while preventing the above described holes from being drilled too deeply which may result in damage to the patella.

With reference now to FIGS. 6 and 7, after the patella has been resected and drilled, the patellar button prosthesis 10 may be installed thereon. For this purpose, a patellar clamp 110 is provided which includes a first lever 111 attached to a housing structure 113 which includes a hole 115 therethrough. A second lever 117 is provided which is pivotally mounted with respect to the lever 111 at the pivot 119 and which reciprocates the plunger 121 with respect to the opening 115, with the opening 115 constraining the plunger 121 to move solely in a linear manner. As seen in FIG. 6, the handle 117 has an end 123 with a knob 125 attached thereto, and the knob 125 rides in a slot 127 formed in the plunger 121 so that as the handle 117 is pivoted with respect to the handle 111, any motion of the portion 123 of the handle 117 which is other than linear with respect to the axis of the opening 115 is of no consequence. As further shown in FIG. 6, an elongated leaf-type spring 129 is attached by a screw 131 to the handle 117 and has an end surface 133 which engages the underside of the handle 111 so as to spring bias the handles 111 and 117 away from one another.

As further shown in FIG. 6, the handle 111 has an eyelet 135 on which is pivotally mounted a threaded member 139 at the pivot 137. The threaded member 139 has threaded thereon a nut 141 having a knurled surface 143 thereon which is provided so as to enable the nut 141 to be rotated so as to reciprocate it in a position enabling the locking of the handles 111 and 117 in a fixed position as for example the position shown in FIG. 6.

With further reference to FIG. 6, the portion 113 of the patellar clamp 110 includes a C-shaped portion having a first region designated by reference numeral 145 which has the opening 115 therethrough. The portion 113 has a second region 147 which faces the opening 115 and has mounted thereon a support member 149 having a part spherical outer shape and a fixation spike 151 protruding upwardly from the central portion thereof. With further reference to FIG. 6, the plunger 121 includes an enlarged head 153 having a recess 155 in a surface 157 thereof which faces the fixation spike 151. Within the recess 155, an O-ring 159 is inserted about the periphery thereof.

The patella clamp 110 is operated as follows:

The patellar button prosthesis 10 is positioned on the patella with the posts 15 thereof engaging the openings of the holes which have been drilled in the resected posterior surface of the patella. The patellar clamp 110 is then centered with the plunger 121 directly over the patellar button prosthesis 10 with the outermost portions of the surface 11 thereof entering the recess 155 as shown in FIG. 6 and engaging the O-ring 159. In this position, the handles 111 and 117 are squeezed which acts to center the fixation spike 151 into the anterior surface of the patella to thereby provide rigid fixation. If desired, the position of the handles 111 and 117 may be fixed through tightening of the nut 141 until it engages the handle 117 to thereby lock the handles 111 and 117 in a pre-determined orientation against the force of the spring 129.

The instruments of the present invention now having been explained, the method of installing a patellar button prosthesis onto a patella utilizing the instruments 20, 70 and 110 is believed to be self evident. The steps are as follows:

(1) An incision is made by the surgeon on the knee in such a manner so as to expose the patella and the adjacent knee structure to view.

(2) After the surgeon has chosen the particular patellar button prosthesis which he or she is going to use, the corresponding wing guide 49, 51 or 53 is pivoted to the position exemplified by the wing guide 49 in FIG. 2. With the appropriate wing guide so positioned, the saw guide is placed over the patella with the appropriate surface in this case 50, of the appropriate wing guide, in this case, 49, engaging the posterior surface of the patella and the jaw members 27 and 29 being oriented in surrounding relation to the periphery of the patella with the teeth 31 thereof engaging the periphery of the patella.

(3) With the saw guide so positioned, the lower guide 57 is pivoted to the position shown in FIG. 2. If the portion 59 thereof engages the anterior surfaces of the patella, then the surgeon knows that he or she has chosen the appropriate sized patellar button prosthesis. If, on the other hand, the portion 59 of the lower guide 57 swings freely without engaging the anterior patellar surfaces, the surgeon then knows that a smaller patellar button prosthesis must be chosen. If the surgeon has secured the saw guide 20 by tightening the nut 45 about the handle 23, the nut 45 is then loosened and the jaw members 27 and 29 are released from the periphery of the patella. Then, the wing guide which was being used is pivoted away from the posterior patellar surface and another wing guide which defines a smaller spacing from the plane of resection is pivoted into place. With this other wing guide then pivoted into place, the saw guide is then reinstalled about the periphery of the patella and after being secured thereto through the use of the nut 45 tightened against the handle 23, and the lower guide 57 is pivoted into the position shown in FIG. 2. If the portion 59 thereof now engages the anterior patellar surfaces, the surgeon will know that the appropriately sized patellar button prosthesis has been chosen. If not, the steps described hereinabove concerning the choosing of a further wing guide, loosening of the saw guide, pivoting of the further wing guide into place and reattaching the saw guide will be followed.

(4) After the saw guide 20 is appropriately fastened to the patella and the surgeon is assured that the appropriately sized patellar button prosthesis has been chosen, a surgical saw is utilized to resect the patella along the plane defined by the posterior surfaces of the jaw member 27 and 29 which plane is referred to by reference numeral 55 in FIG. 2. In order to accurately accomplish the resection, the saw blade is allowed to engage the posterior surfaces of the jaw members 27 and 29 at the plane 55 throughout the resection.

(5) After the resection is completed and the posterior portion of the patella is removed, the drill guide 70 is attached to one of the jaw members 27 or 29 of the saw guide 20 as shown, for example, in FIG. 3. The precise position of the template 73 thereof is set utilizing the structure more particularly shown in FIG. 4 and as described hereinabove so as to center the drill guide 70 over the available bone.

(6) With the drill guide 70 so positioned, a drill bit such as the drill bit 100 shown in FIG. 5 is attached to the surgical drill and the end, 101 of the drill bit is inserted through one of the holes 93 in the template 73 and a hole is drilled in the patella whereafter the drill bit 100 is inserted into the other hole 93 and the other hole is drilled. The interaction between the collar 105 of the drill bit 100 and the surface 74 of the template 73 defines the axial extent to which the portion 101 of the drill bit will extend through the holes 93. This in conjunction with the location of the template 73 centered with respect to the jaws 27 and 29, which is defined by the mechanism best seen in FIG. 4 which mounts the drill guide 70 to one of the jaw members 27 or 29 defines the axial extent to which the end 101 of the drill bit 100 will extend into the patella during the drilling process, thereby providing a safeguard against the drilling of holes in the patella which are deeper than necessary.

(7) After the holes have been drilled in the posterior surface of the patella, the drill guide 70 may be removed from the jaw member of the saw guide 20 and the saw guide may be removed from the periphery of the patella although this step may be carried out without removing the saw guide. With the drill guide and saw guide (optionally) removed, the patellar clamp shown in FIGS. 6 and 7 may then be utilized to install the patellar button prosthesis 10 onto the flat posterior surface of the patella. As explained hereinabove, the patellar button prosthesis 10 is positioned on the patella with the posts 15 thereof just entering the holes drilled in the posterior surface of the patella. In this position, the plunger 121 is centered over the patellar button prosthesis 10 with the spherical surface 11 thereof entering the recess 155 and engaging the O-ring 159. In this position, the patellar clamp 110 is compressed by squeezing of the handles 111 and 117 to thereby center the fixation spike 151 in the anterior surfaces of the patella to thereby provide rigid fixation. The patellar clamp 110 may be locked into this position by threading the nut 141 to the position shown in FIG. 6 bearingly engaging the handle 117.

(8) After the patellar clamp 110 has been appropriately removed from the patella, and the surgeon is satisfied that the patellar button prosthesis 10 has been properly installed, the surgeon may close the incision.

Accordingly, an invention has been disclosed herein which is embodied in several instruments usable in combination to practice a method of installing a patellar button prosthesis on the posterior surface of a patella which has been resected in accordance with the teachings of the present invention. It should be understood, that various modifications, alterations, changes and reconfigurations of the instruments disclosed hereinabove and the method practiced through the use of the instruments described hereinabove may be made without departing from the teachings of the present invention. It is intended that the present invention only be limited by the terms of the appended claims.

I claim:

1. A patellar clamp for installing a patella button on a resected posterior surface of a patella, comprising:
 (a) a body portion including a first handle fixedly extending therefrom, said body portion including a C-shaped structure having a bottom surface and a top opening;
 (b) said bottom surface having a convex surface with a fixation spike extending upwardly therefrom substantially centrally located thereon;
 (c) said top opening comprising one end of a linear bore through said body portion which is substantially coaxial with said fixation spike;
 (d) a second handle pivotably mounted to said body portion;
 (e) a plunger extending through said bore and including a first end facing said fixation spike and a second end with a slot receiving a distal end of said second handle;
 (f) whereby pivotal movement of said second handle with respect to said first handle causes linear reciprocation of said plunger in said bore.

2. The invention of claim 1, further including a spring interposed between said handles.

3. The invention of claim 1, wherein said plunger first end includes a head having a recess facing said fixation spike, said convex surface being part spherical.

4. The invention of claim 3, further including a seal at the periphery of said head recess.

5. The invention of claim 2, further including locking means for locking the position of said handles against the force of said spring.

6. The invention of claim 5, wherein said locking means comprises a threaded member having a first end pivotably mounted to said first handle and a second end extendable through a proximal opening in said second handle, and locking means for selectively locking said handles at a predetermined desired separation.

* * * * *